US010517524B2

(12) United States Patent
Garnavi et al.

(10) Patent No.: US 10,517,524 B2
(45) Date of Patent: Dec. 31, 2019

(54) MINING SOCIAL MEDIA FOR ULTRAVIOLET LIGHT EXPOSURE ANALYSIS

(71) Applicant: International Business Machines Corporation, Armonk, NY (US)

(72) Inventors: Rahil Garnavi, Macleod (AU); Timothy M. Lynar, Kew Vic (AU); Suraj Pandey, Melbourne (AU); Ziyuan Wang, Malvern (AU); John M. Wagner, Plainville, CT (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/299,249

(22) Filed: Mar. 12, 2019

(65) Prior Publication Data
US 2019/0209075 A1    Jul. 11, 2019

Related U.S. Application Data

(63) Continuation of application No. 15/296,285, filed on Oct. 18, 2016, now Pat. No. 10,265,011, which is a continuation of application No. 14/133,799, filed on Dec. 19, 2013, now Pat. No. 9,554,744.

(51) Int. Cl.
*G06K 9/00*   (2006.01)
*A61B 5/00*   (2006.01)
(Continued)

(52) U.S. Cl.
CPC ............ *A61B 5/444* (2013.01); *A61B 5/1032* (2013.01); *A61B 5/445* (2013.01); *A61B 5/7275* (2013.01);
(Continued)

(58) Field of Classification Search
CPC .......... G06K 9/00885; G06K 9/00892; G06K 9/00604; G06K 9/0061; G06K 9/00617;
(Continued)

(56) References Cited

U.S. PATENT DOCUMENTS 6,204,064 B1 * 3/2001 Alberts ................. G01N 33/48
382/128
7,110,597 B2 * 9/2006 Goldsmith ........... H04N 1/6027
348/E9.04
(Continued)

FOREIGN PATENT DOCUMENTS

WO        2013034288        3/2013

OTHER PUBLICATIONS

US 8,548,214 B2, 10/2013, Calman et al. (withdrawn)
(Continued)

*Primary Examiner* — Avinash Yentrapati
(74) *Attorney, Agent, or Firm* — Fleit Intellectual Property Law; Jon Gibbons

(57) ABSTRACT

Social media databases are minded for data related to a subject person. The data in indicative of a level of ultraviolet light exposure of the subject person. An ultraviolet violet exposure profile for the subject person is generated based upon the data and a health assessment report provided. The data may include timestamped images of the subject person and other related persons. The skin characteristics within images are analyzed to determine an ultraviolet light exposure level for the subject person from each image. The skin characteristics may include skin color, freckling and blemishing. The ultraviolet light exposure profile may be developed over an extended interval based upon the image timestamps. The health report may be used to mitigate risks, such as skin cancer, associated with exposure to ultraviolet light.

19 Claims, 7 Drawing Sheets

(51) Int. Cl.
| | |
|---|---|
| *G16H 50/30* | (2018.01) |
| *G16H 15/00* | (2018.01) |
| *G16H 50/20* | (2018.01) |
| *G16H 10/60* | (2018.01) |
| *G06Q 50/00* | (2012.01) |
| *G06F 19/00* | (2018.01) |
| *G06Q 30/02* | (2012.01) |
| *A61B 5/103* | (2006.01) |
| *G16H 40/67* | (2018.01) |
| *G06T 7/00* | (2017.01) |

(52) U.S. Cl.
CPC .............. *A61B 5/742* (2013.01); *A61B 5/746* (2013.01); *G06F 19/3418* (2013.01); *G06Q 30/0201* (2013.01); *G06Q 50/01* (2013.01); *G16H 10/60* (2018.01); *G16H 15/00* (2018.01); *G16H 40/67* (2018.01); *G16H 50/20* (2018.01); *G16H 50/30* (2018.01); *G06T 7/0012* (2013.01)

(58) Field of Classification Search
CPC .......... G06K 2009/00328; G06K 2009/00322; G06K 9/00221; G06K 9/00228; G06K 9/00234; G06K 9/00241; G06K 9/00248; G06K 9/00255; G06K 9/00261; G06K 9/00268; G06K 9/00275; G06K 9/00281; G06K 9/00288; G06K 9/00295; G06K 9/00302; G06K 9/00308; G06K 9/00315; A61B 5/1176; G06F 17/30793; G06T 2207/30201; H04N 1/00336; H04N 5/23219

See application file for complete search history.

(56) References Cited

U.S. PATENT DOCUMENTS

| | | | | |
|---|---|---|---|---|
| 8,238,623 | B2* | 8/2012 | Stephan | A61B 5/442 382/100 |
| 2002/0154793 | A1* | 10/2002 | Hillhouse | G06K 9/00087 382/115 |
| 2003/0065523 | A1* | 4/2003 | Pruche | A45D 44/005 382/118 |
| 2003/0087333 | A1* | 5/2003 | Hirai | G01N 1/30 435/40.5 |
| 2004/0125996 | A1* | 7/2004 | Eddowes | A61B 5/0059 382/128 |
| 2005/0058709 | A1* | 3/2005 | Fisher | A61K 8/35 424/468 |
| 2005/0195316 | A1* | 9/2005 | Kollias | G03B 29/00 348/370 |
| 2007/0064989 | A1* | 3/2007 | Chhibber | A61B 5/442 382/128 |
| 2007/0073113 | A1* | 3/2007 | Squilla | A61B 5/00 600/300 |
| 2007/0086651 | A1* | 4/2007 | Stephan | A61B 5/442 382/162 |
| 2009/0059028 | A1* | 3/2009 | Kollias | A61B 5/0071 348/222.1 |
| 2009/0185727 | A1* | 7/2009 | Beckmann | A61B 5/1171 382/128 |
| 2009/0239254 | A1* | 9/2009 | Duval | C12N 5/0698 435/29 |
| 2009/0245603 | A1* | 10/2009 | Koruga | A45D 44/00 382/128 |
| 2010/0173024 | A1* | 7/2010 | McDaniel | A61K 31/05 424/729 |
| 2010/0189313 | A1* | 7/2010 | Prokoski | A61B 5/0064 382/118 |
| 2010/0309300 | A1* | 12/2010 | Chhibber | A61B 5/0059 348/77 |
| 2010/0316296 | A1* | 12/2010 | Chhibber | G06F 19/321 382/190 |
| 2011/0206254 | A1* | 8/2011 | Patwardhan | A61B 5/0077 382/128 |
| 2011/0211736 | A1* | 9/2011 | Krupka | G06K 9/00677 382/118 |
| 2012/0230540 | A1* | 9/2012 | Calman | G06K 9/00221 382/103 |
| 2013/0065781 | A1* | 3/2013 | Terunuma | C12Q 1/6883 506/9 |
| 2013/0104080 | A1 | 4/2013 | Bosworth et al. | |
| 2013/0141235 | A1* | 6/2013 | Utter, II | G08B 21/02 340/539.12 |
| 2013/0265450 | A1* | 10/2013 | Barnes, Jr. | H04N 5/77 348/207.1 |
| 2013/0273968 | A1* | 10/2013 | Rhoads | G06K 9/6253 455/556.1 |
| 2014/0002342 | A1* | 1/2014 | Fedorovskaya | G06Q 30/0271 345/156 |
| 2014/0201126 | A1* | 7/2014 | Zadeh | G06N 7/005 706/52 |
| 2014/0223462 | A1* | 8/2014 | Aimone | A61B 5/0476 725/10 |
| 2014/0270407 | A1* | 9/2014 | Balakrishnan | G06K 9/00275 382/118 |
| 2015/0016693 | A1* | 1/2015 | Gattuso | H04N 5/23219 382/118 |
| 2015/0049910 | A1* | 2/2015 | Ptucha | G06F 16/51 382/103 |
| 2015/0178915 | A1* | 6/2015 | Chatterjee | G06K 9/20 382/128 |
| 2015/0178920 | A1* | 6/2015 | Garnavi | G16H 50/30 600/476 |
| 2015/0242707 | A1* | 8/2015 | Wilf | G06K 9/00302 382/159 |

OTHER PUBLICATIONS

Skin Cancer Foundation, "Melanoma Causes and Risk Factors", http://www.skincancer.org/skin-cancer-information/melanoma/melanoma-causes-and-risk-factors, last visited on Jul. 28, 2017, p. 1.

Skin Cancer Foundation, "Basal Cell Carcinoma", http://www.skincancer.org/skin-cancer-information/basal-cell-carcinoma, last visited on Jul. 28, 2017, pp. 1-2.

Skin Cancer Foundation, "Squamous Cell Carcinoma", http://www.skincancer.org/skin-cancer-information/squamous-cell-carcinoma/scc-causes-and-risk-factors, last visited on Jul. 28, 2017, pp. 1-2.

Burnett, M., et al., "Current sunscreen controversies: a critical review", Photodermatology, Photoimmunology & Photomedicine, Apr. 2011, vol. 27, No. 2, pp. 1-10.

Kanavy, H., et al., "Ultraviolet Radiation and Melanoma", Seminars in Cutaneous Medicine and Surgery, Dec. 2011, vol. 30, No. 4, pp. 1-7.

Millen, A., et al., "Diet and Melanoma in a Case-Control Study", Cancer Epidemiology, Biomarkers & Prevention, Jun. 2004, pp. 1-11.

The American Cancer Society, "Risk factors for melanoma skin cancer", http://www.cancer.org/cancer/skincancer-melanoma/detailedguide/melanoma-skin-cancer-risk-factors, last visited on Jul. 28, 2017, pp. 1-4.

Aim at Melanoma Foundation, "Top 17 Risk Factors for Melanoma", https://www.aimatmelanoma.org/melanoma-risk-factors/, last visited on Jul. 28, 2017, pp. 1-5.

Centers for Disease Control and Prevention, "What are the risk factors for skin cancer?", http://www.cdc.gov/cancer/skin/basic_info/risk_factors.htm, last visited on Jul. 28, 2017, pp. 1-2.

Vitamin D Wiki, "Prototype armband measures amount of UV—Oct. 2010", http://www.vitamindwiki.com/Prototype+armband+measures+amount+of+UV+-+Oct+2010 Oct. 28, 2010, pp. 1-6.

amazon.com, "Portable UV Checker Atmospheric Light Meter", http://www.amazon.com/Portable-Checker-Atmospheric-Light-Meter/dp/B00481APE8/ref=pd_cp_hi_1, last visited on Jul. 28, 2017, pp. 1-6.

(56) References Cited

OTHER PUBLICATIONS

Lumalier, "X-9", http://www.lumalier.com/index.php?option=com_k2&view=item&id=10, last visited on Jul. 28, 2016, p. 1.
amazon.com, "UV HAWK Q3I-UVHAWK Ultraviolet Share Sunlight Meter", https://www.amazon.com/Q3I-UVHAWK2-Waterproof-Ultraviolet-Sunlight-Meter/dp/B001Q3KW4O/ref=sr_1_fkmr0_1?ie=UTF8&qid=1473181251&sr=8-1-fkmr0&keywords=UV+HAWK+Q3I-UVHAWK+Ultraviolet+Share+Sunlight+Meter, last visited on Jul. 28, 2016, pp. 1-4.
Amini, N., et al., "A Wireless Embedded Device for Personalized Ultraviolet Monitoring", Proceedings of Biodevices 2009, Jan. 14-17, 2009.
Constine, J., "Facebook Patents Point to an All-Seeing, All-Hearing Instagram Video" https://techcrunch.com/2013/07/07/instagram-is-listening/, last visited on Jul. 28, 2016, page.
Constine, J., "Facebook's New Colocation and Image Recognition Patents Tease the Future of Sharing".
Khaparde, A., et al., "Face Detection Using Color Based Segmentation and Morphological Processing—A Case Study", Bharath Institute of Science and Technology, 2012.
Cokkinides, Vilma, et al., "Trends in Sunburns, Sun Protection Practices, and Attitudes Toward Sun Exposure Protection and Tanning Among US Adolescents," Pediatrics Official Journal of the American Academy of Pediatrics, Pediatrics 2006; 118, 853-864, DOI: 1542/peds.2005-3109.
Ilea, Dana E., et al., "CTex—An Adaptive Unsupervised Segmentation Algorithm Based on Color-Texture Coherence," IEEE Transactions on Image Processing, vol. 17, No. 10, Oct. 2008, 1057-7149, copyright 2008 IEEE.
Khaparde, A., et al., "Face Detection Using Color Based Segmentation and Morphological Processing—A Case Study," White Paper, Date Not Available.vv.
Mahler, H.I., et al., "Effects of UV Photograph, Photoaging Information, and Useof Sunless Taning Lotion on Sun Protection Behaviors," Reprinted Arch Dermato/vol. 141, Mar. 2005, copyright 2005 American Medical Association.
Tadokoro, T., et al., "Mechanisms of Skin Tanning in Different Racial/Ethnic Groups in Response to Ultraviolet Radiation," J Invest Dermatol 124:1326-1332, copyright 2005 by The Society for Investigative Dermatology, Inc.
Travers, Robin U., MD, "Social Media in Dermatology: Moving to Web 2.0," Seminars in Cutaneous Medicine and Surgery, vol. 31, No. 3, 1085-5629/12, copyright 2012, published by Elsevier, Inc.
List of IBM Patents or Applications Treated as Related.

* cited by examiner

MINING SOCIAL MEDIA FOR ULTRAVIOLET LIGHT EXPOSURE ANALYSIS

BACKGROUND

This disclosure broadly relates to the field of determining levels of exposure of an individual to ultraviolet light, and more particularly to the field of analyzing social media data to determine such levels of exposure.

Skin cancer is a cancer that forms in the tissues of the skin when skin cells are damaged, including by overexposure to ultraviolet light from the sun. There are three main types of skin cancer, named after the type of skin cell from which they arise: melanoma, which forms in melanocytes, the skin cells that make pigment; basal cell carcinoma, which forms in the lower part of the epidermis, the outer layer of the skin; and squamous cell carcinoma, which forms in squamous cells, the flat cells that form the surface of the skin. Of these three, melanoma is the least common skin cancer, but also is the most aggressive, the most likely to spread and, if left untreated, fatal. Sun exposure is a significant risk factor for all three types of skin cancer. There are many other risk factors, including personal and family histories; skin and hair color; and even eye color. Other risk factors include moles and immune system strength.

Skin cancer is the most common of all cancers, accounting for nearly half of all cancers in the United States; more than 3.5 million skin cancers are diagnosed annually in more than 2 million people, with melanoma accounting for more than 75,000 cases and over 8,500 deaths. About one in five Americans will develop skin cancer in their lifetime, and about one in 50 Americans will develop melanoma in their lifetime. Skin cancer is also not limited to the elderly: melanoma is the most common form of cancer for young adults 25-29 years old and the second most common form of cancer for adolescents and young adults 15-29 years old. One person dies of melanoma every 57 minutes. Skin cancer also accounts for many billions of dollars in both direct and indirect spending. In the United States, according to the National Cancer Institute, the total direct costs associated with the treatment for non-melanoma skin cancer in 2004 was $1.5 billion, and the estimated total direct cost associated with the treatment of melanoma in 2010 was $2.36 billion.

Exposure to ultraviolet light from the sun can not only result in skin cancer but also can result in changes in skin characteristics such as skin color or tan, freckling, and skin blemishes. Such changes are often recorded in images that may be stored on social media databases or web sites. Such databases are able to accumulate numerous images over an extended period of time. Analysis of an ultraviolet light exposure profile may be beneficial in mitigating harm caused by exposure to ultraviolet light exposure.

SUMMARY

A method comprises receiving a multiplicity of images from an at least one remote database; analyzing the multiplicity of images to determine an ultraviolet light exposure profile of a subject person; and generating a health assessment report for the subject person based upon the ultraviolet light exposure profile.

A computer storage program product comprises a storage medium readable by a processing circuit and storing instructions for execution by the processing circuit configured to perform a method comprising: receiving a multiplicity of images from an at least one remote database; analyzing the multiplicity of images to determine an ultraviolet light exposure profile of a subject person; and generating a health assessment report for the subject person based upon the ultraviolet light exposure profile.

A device comprises a data receiver configured to receive a multiplicity of images recorded with visible light, the multiplicity of images received from a plurality of social media databases; a subject person identifier configured to analyze the multiplicity of images to identify a plurality of subject person images including a subject person having a skin color that varies with exposure to ultraviolet light; a skin color determiner configured to determine a skin color of the subject person within each of the subject person images; an ultraviolet light exposure determiner configured to generate a multiplicity of data points corresponding to the multiplicity of images, each data point corresponding to an ultraviolet light exposure level for each of the subject person images determined based upon the skin color of the subject person within each of the subject person images; a multiple photo analyzer configured to generate an ultraviolet light exposure profile for the subject person based upon the multiplicity of data points; and a report generator configured to generate a health assessment report for the subject person based upon the ultraviolet light exposure profile, the health assessment report including an ultraviolet light exposure risk assessment for the subject person.

BRIEF DESCRIPTION OF THE DRAWINGS

The accompanying figures where like reference numerals refer to identical or functionally similar elements throughout the separate views, and which together with the detailed description below are incorporated in and form part of the specification, serve to further illustrate various embodiments and to explain various principles and advantages all in accordance with the present disclosure, in which.

DETAILED DESCRIPTION

Figure 1:
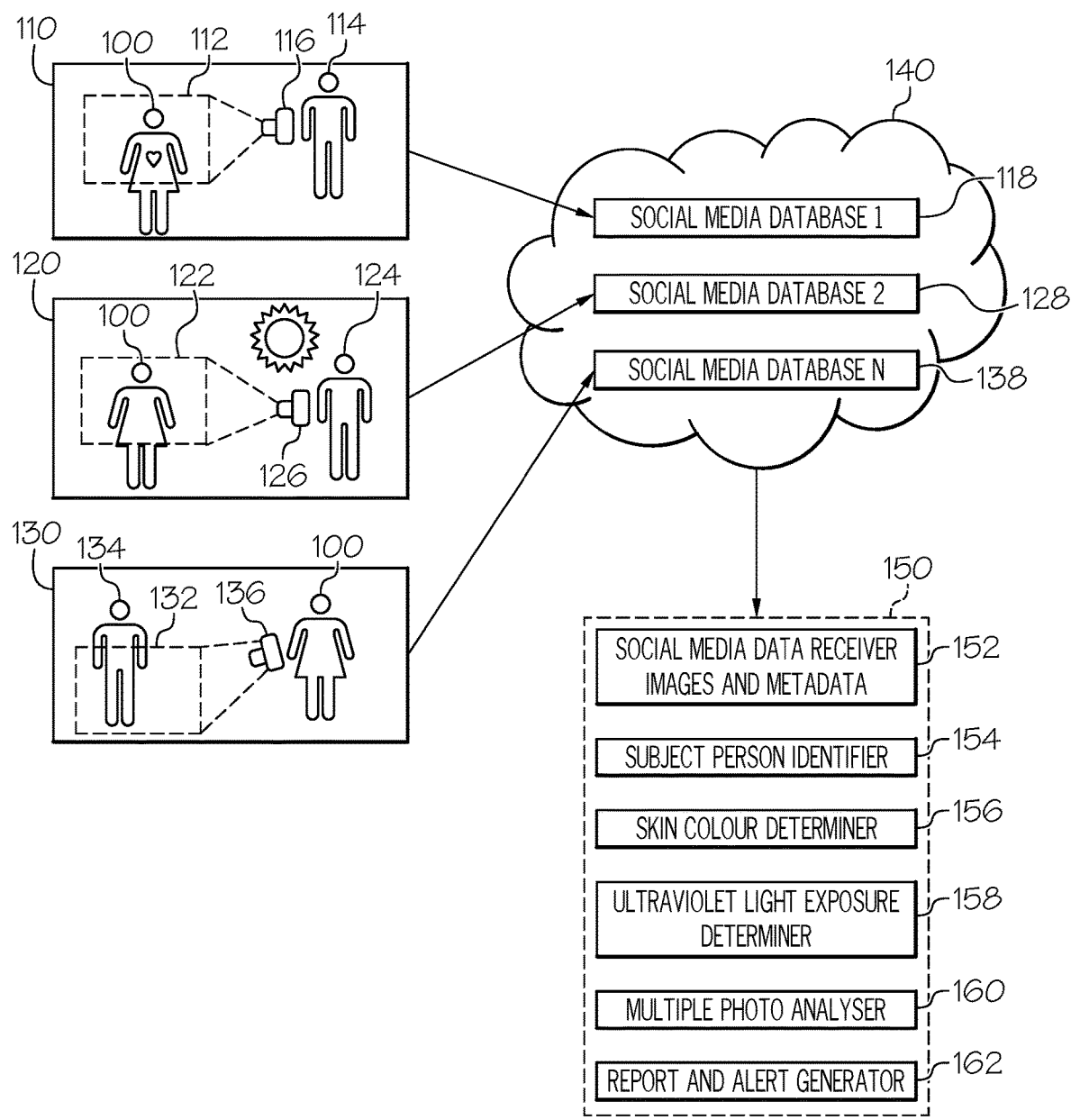
FIG. 1 illustrates a system in which a device generates a report based upon a subject person's exposure to ultraviolet light, the ultraviolet light exposure being based upon data received from multiple social media databases.

In the following discussion, details are provided to help thoroughly understand the present disclosure. However, it is apparent to those of ordinary skill in the art that even though there may be no such details, the understanding of the present disclosure would not be influenced. In addition, it should be further appreciated that any specific terms or applications used herein are only for the convenience of description, and thus the present disclosure should not be limited to only use in any specific terms or applications represented and/or implied by such terms.

Generally speaking, images and image metadata posted on social media databases including other online image galleries are analyzed to track changes over time of hair color, and skin color, skin tone, blemishes and lesions to produce a health assessment report which may allow for estimates of the risk of development of skin diseases including melanoma, basal cell carcinoma and squamous cell carcinoma. A model of ultraviolet light exposure, based upon the images is related to the risk of development of these skin diseases. The health assessment report may be used to predict general aspects of a person's lifestyle. Also, ultraviolet light exposure and lifestyle attributes may be implied or inferred based upon the ultraviolet light exposure and lifestyle attributes of linked or related individuals within social networks.

People have used their private social circles to share images of themselves and others for decades. With the recent proliferation of social networking sites, such as Facebook.com, Twitter.com, weibo.com, renren.com, and the advent of consumer cameras able to easily upload recorded images to the social networking sites, the sharing of pictures has become easier and more common. In addition to the images themselves, people also share significant metadata, including timestamps and location data, attached to those images, e.g. in image descriptions on Facebook or in tweets on Twitter. Most of these social networking sites also have the capability to tag or label others in their network. This feature enables tracking of the changes people undergo by collecting the images of a person and analyzing changes over time of hair color, and skin color, tone, blemishes and lesions. As a simplified description, the processes involves mining social media sites to collect pictures of a subject person under analysis/search, generating a color segmented image with timestamps information obtained from the metadata, analyzing the color segmented images and build a ultraviolet light exposure profile of a subject person over time, analyzing the color segmented images and build a ultraviolet light exposure profile of the people related to the subject person under analysis, and building a relative ultraviolet light exposure profile of the subject and associated people.

Mining social media sites to collect pictures of a subject under analysis/search includes a search of image data that are tagged with the subject's information (name, nick name, address, workgroup, fun group, etc.) within social networking sites. The search task can be performed using the links the subject has with their friends and relatives, as done by Facebook and Twitter when searching for known circle of friends. Generating a color segmented image with timestamps information obtained from the metadata (e.g., the date the image was tagged or uploaded) involves creating segmented images of the search results, where the segmentation is primarily done on color and tone. For example, a tanned person could be relatively darker in the images taken during summer times as compared to when the person was indoors during colder seasons. This step also involves collecting metadata of the images, such as the time and place the image was taken, and associating the images with the metadata. The processes includes analyzing the color segmented images and building an ultraviolet light exposure profile of a person over time involves the process of image analysis, where the color segmented images are sorted in time (e.g., summer, winter) and space (e.g., beach, indoors, parties, etc.) and a ultraviolet light exposure profile is built. The ultraviolet profile clearly helps describe when, where, how, and to what extent the person changed their skin color and tone as a result of ultraviolet light exposure. Analyzing the color segmented images and building a ultraviolet light exposure profile of the people related to the subject person under analysis involves the process of inferring, based upon both image analysis and social links, the ultraviolet light exposure profile of people related to or otherwise linked to the subject person. For instance, a couple holidaying around beaches could potentially have the same ultraviolet light exposure profile during the holiday time, although only one of them posted their image to the social media. The posted images may or may not have the subject person within them. Building a relative ultraviolet light exposure profile of the subject and related people analyzes people who are not in the pictures, but are related to the subject under analysis. This relationship could be a permanent one (e.g., marriage), seasonal (e.g., holiday friends), or other social links that are determined by online social interactions. Then, the ultraviolet light exposure level of the related person can be applied to the subject person.

The images of the present description are primarily recorded with visible light. An image recorded with visible light includes images recorded from light in the visible light spectrum and excludes images captured primarily with ultraviolet light and images captured primarily with infrared light. An image recorded with visible light include images captured with ambient light, sunlight and flash photography. An image recorded with visible light is intended to have subject matter that appears substantially identical to a scene perceived by an observer having viewed the subject matter when the image was recorded.

A related person has an identifiable relationship with the subject person wherein the ultraviolet light exposure of the subject person may be synthesized from the determined ultraviolet light exposure of the related person. In one example the related person may be a relative of the subject person, such as the spouse, parent, child or sibling. In another example, the related person may be included in an image recorded by the subject person. In another example, the related person may be known to spend time with the subject person, such as team mates or travel companions. The relationship may be predetermined and designated by the subject person or may be determined from metadata included with the images, the metadata indicative of the relationship.

FIG. 1 illustrates a system in which a device generates a report in based upon a subject person' exposure to ultraviolet light, the ultraviolet light exposure being based upon data received from multiple social media databases. During event 110, a subject person 100 is included in a recorded image 112 taken by a first camera operator 114 operating a first camera 116. The first camera 116 may, in this example, be a "point-and-shoot" pocket camera. Data associated with event 110 is stored on first social media database 118, which in one example may be a social media database such as the database maintained by the Facebook social media service. Event 110 may occur at a first time during a first season, for example the season may be winter and the time may be February 14. The data associated with the event includes information from which the subject person's exposure to ultraviolet light may be determined. Such data may include the image 112 recorded by the camera 116 and may include the skin color or amount of tan of the subject person. In another example, the data may include information which may be indicative of a level of ultraviolet light exposure. For example the data may include a message indicating that the subject person has been indoors for an extended period because of inclement winter weather: accordingly, it may be determined that the subject person has received almost no ultraviolet light exposure.

During event 120, the subject person 100 is included in a recorded image 122 taken by a second camera operator 124 operating a second camera 126. The second camera may, in this example, be a digital signal lens reflex (DSLR) camera recording images using natural lighting or other form of visible light illumination. Data associated with event 120 may be stored on a second social media database 128, which in one example may be a social media database such as the database maintained by the Google social media service. Event 120 may occur at a second time during a second season, for example the season may be spring and the time may be April 1. The data associated with the event includes information from which the subject person's exposure to ultraviolet light may be determined. Such data may include the image 122 recorded by the camera 126 and may include the skin color or amount of tan of the subject person at the time of the image recording. The data may include information which may be indicative of a level of ultraviolet light exposure. For example the data may include a message indicating that the subject person is enjoying spending lunches in the sunlight: accordingly, this additional information may be used to determine that the subject person is receiving regular exposure to ultraviolet light.

During event 130, the subject person 100 is recording an image 132 of a related person 134 taken by a third camera 136. The third camera may, in this example, be a cell phone camera belonging to or otherwise associated with the subject person 100. Data associated with event 130 may be stored on a third social media database 138, which in one example, may be a social media database such as the database maintained by the MySpace social media service. Event 130 may occur at a third time during a third season, for example the season may be summer and the time may be July 4. The data associated with the event includes information from which the subject person's exposure to ultraviolet light may be determined. Such data may include the image 132 recorded by the camera 136 and may include the skin color or amount of tan of the related person at the time of the image recording. In one example, the data may include an image of a foot of the subject person with sandals removed after a day in the sun. Sandals block portions of the skin from ultraviolet light exposure and thus have a different skin color than areas of the skin which have received ultraviolet light exposure. The data may include information which may indicate that the person in the photo is related to the subject person and thus the determined level of ultraviolet light exposure of the related person may be applied to the subject person. The relationship between the subject person and the related person may be determined in any of a number of ways. For example, image 132 was recorded with the cell phone camera of the subject person, and thus the relationship may be established. In another example, the metadata associated with image may indicate the relationship, for example the image may include information identifying the person in the image as a spouse or companion of the subject person, or may include a message indicating that the subject person has spent the day with the person in the image. Thus, the data associated with event 130 includes information indicative of a level of ultraviolet light exposure of the subject person. For example the data may include a message indicating that the subject person is associated with the related person even though the subject person is not included in an image associated with event 130.

Cameras 116, 126 and 136 may be typical cameras used to capture a multiplicity of images recorded primarily with visible light, such that the recorded image appears substantially the same as the image viewed by the unaided eye when the image was recorded using light primarily in the visible spectrum. One intended purpose of recording each image is to allow those accessing the social media databases to share in the experience of the events from which the images were recorded while also building an ultraviolet light exposure of a subject person. This intended purpose has nothing to do with the analysis of ultraviolet light exposure levels of the subject person. Thus, the camera and lighting of the recorded images do not unduly skew the recorded images towards the ultraviolet or infrared spectrums. Such skewing may require specialized cameras and lighting and may produce images that appear substantially different from the appearance of the event as seen by the unaided eye when the event is illuminated primarily with visible light, and would detract from an intended purpose of the recording of the images. Furthermore, requiring use of such specialized cameras and lighting skewed towards the ultraviolet or infrared spectrum may significantly reduce the availability of images of the subject person available on social media databases, thereby hampering the amount of available data and long term analysis of ultraviolet light exposure of the subject person. Furthermore, the dissimilarity of the image recorded with light primarily above or below the visible spectrum distorts the appearance of the persons in the image in a way that tends to detract from the use of the image for social media communications.

Social media databases 118, 128 and 138 include a plurality of social media databases that are remote databases that are not necessarily hosted by device 150. The remote databases may be included in a cloud 140 which may be accessed by device 150 through the internet or other network for receiving data and images 112, 122, 132 from events 110, 120, and 130. Images 112 and 122 comprise a plurality of subject person images including a subject person having a skin color that varies with exposure to ultraviolet light. Image 132 include a related person image. The social media databases may also be accessed by device 150 using the internet or other network to access the cloud 140. In one example, the images may be stored on a single social media database. In another example, several social media databases may include several images or other data indicative of an ultraviolet light exposure level of the subject person.

Device 150 corresponds to a digital processing machine and includes a computerized device able to access the cloud 140 and data stored on remote social media databases 118, 128 and 138. The computerized device may include any of a number of different devices including a server, a desktop computer, a laptop computer, a tablet, and a cellphone. Device 150 includes a social media data receiver 152 that receives data including images and metadata from at least one remote social media database. The data is then analyzed by subject person identifier 154 to determine if any of the data identifies the subject person. The analysis may include examining the data for names and other data segments such as phone numbers used to identify the subject person. If the data includes images such as a photograph or a video recording, then facial recognition may be employed to identify if the subject person is included in the image. Also, metadata associated with the image may be analyzed to identify the subject person. Other methods of determining if data is to be associated with the subject person include determining if the data comes from an account assigned to the subject person, or from an account of a person related to the subject person, such as a spouse, partner or companion of the subject person. Other methods of determining if data is associated with the subject person or identifies the subject person may be implemented while remaining within the scope of this description.

If the data includes an image, be it a photograph, video recording or other image recorded primarily with visible light, then the color of the skin of the subject person or person related to the subject person is determined by skin color determiner 156. This may be done by selecting an area of skin exposed to sunlight and determining its color by analyzing the area using color segmentation. For example, if the face of the subject person or related person is to be analyzed, the area of skin exposed to sunlight could be the forehead area of the face, or the darkest area of skin of the face. One example of color segmentation known to those familiar with the art includes decomposing the images into red, green and blue (RGB) components, another example includes hue, saturation and lightness (HSL). Other processes such as white balance or other compensation methods may also be employed to account for different lighting, camera settings, and image capturing phenomena known to those familiar with the art, to obtain a more consistent color segmentation determination from image to image.

Ultraviolet light exposure determiner 158 determines an amount of ultraviolet light exposure of a person from data received from a social media database and a corresponding data point corresponding to the ultraviolet light exposure level. If the data is from the skin color of an image, then the ultraviolet light exposure may be determined from the skin color in any of several ways. In one example, a known relationship between skin color and average ultraviolet light exposure is established based upon prior determinations or attributes of the person recorded in the image. In another example, skin color of an area of skin exposed to ultraviolet light is compared to a skin color of an unexposed area of skin that has been less exposed to ultraviolet light of the person. In one example the exposed and unexposed areas of skin may be in a single image, in another example, the exposed and unexposed areas of skin may be in different images recorded at different times: for example, an unexposed area may be recorded in winter where the person spends significant time indoors free of ultraviolet light exposure and the exposed area may be recorded in summer where the person spends significant time outdoors and receives exposure to ultraviolet light.

The ultraviolet light exposure determiner may also analyze social media data to qualify its determination based upon the behavior of the subject person. For example, if the data indicates the person has received a chemical tan, a chemical spray, or a "spray tan" of chemicals that color the skin to provide the appearance of a tan received by ultraviolet light exposure, then the ultraviolet light exposure determination made by image processing may be modified, reduced, discounted, given less weight or even eliminated. If the data indicates the person has visited a tanning booth during winter, thereby receiving exposure to ultraviolet light without being exposed to sunlight, then any unexposed determination may be accordingly discounted or given less weight. Other behaviors include a spending a time at a vacation location, participation in an outdoor sport, visiting ultraviolet tanning salon, all of which have characteristic ultraviolet light exposure attributes which may be used to qualify the ultraviolet light exposure determination. Ultraviolet light exposure determiner 158 may also determine ultraviolet light exposure even if the data does not include a recorded image. For example if the data is a calendar appointment indicating the person will spend two hours surfing on a certain beach at a certain time, then exposure to ultraviolet light determination may be made accordingly. Furthermore, ultraviolet light exposure by sunlight may vary depending upon the weather, thus the weather report and other atmospheric conditions for the beach at the time may be analyzed to determine the level of ultraviolet light received from the sun by the during the calendar appointment.

Multiple photo analyzer 160 then analyzes a multiplicity of photos over a time span to determine an ultraviolet light exposure profile of the subject person based upon the data points determined by the ultraviolet light exposure determiner 158. Since the social media databases accumulate images and other data related to the subject person, the images captured by the subject person and as well as others, over many years, the data may be mined to obtain a long term determination of the ultraviolet light exposure profile of the subject person. Thus, what is shown is an example of analyzing, by a digital processing machine, the multiplicity of images to transform the multiplicity of images into an ultraviolet light exposure profile of a subject person. Report and alert generator 162 then generates a report based upon the profile and may also generate an alert if the profile shows a developing health risk. The report and/or alert may be provided to the subject person, a person related to the subject person or a doctor or attending physician to be used in counseling the subject person on health related matters. The health assessment report includes an ultraviolet light exposure risk assessment for the subject person. The health assessment report may include a risk related to skin cancers and other skin maladies, as well as advice for mitigating the risk.

FIG. 2, FIG. 3, FIG. 4 and FIG. 5 show examples of skin color of images of a subject person based upon exposure to ultraviolet light. The images are recorded over a period of time and may be mined from one or more social media databases. For example, the image of FIG. 2 may have been recorded in winter where the subject person spent most of the time indoors, not exposed to ultraviolet light from the sun; the image of FIG. 3 may have been recorded in spring where the subject person spent some time in the sun, received some exposure to ultraviolet light; the image of FIG. 4 may have been recorded in late summer where the subject person spent more time in the sun, receiving more exposure to ultraviolet light; and the image of FIG. 5 may have been recorded in midsummer after a day where the subject person spent a long amount of time in the sun, receiving excessive exposure to ultraviolet light resulting in a sunburn.

To provide examples of skin color of recorded images, a red green blue (RGB) color scale is used to segment the image into colors. The scale for each color spans from 0 to 255 with an RGB of (0, 0, 0) corresponding to black and an RGB of (255, 255, 255) corresponding to white. Using this scale, the RGB color of the portion of the image of FIG. 2 including the skin color of the subject person may be (255, 245, 235). This RGB color corresponds to the subject person having skin with a light color, the light color being indicative of little or no sun tan. In this example, based upon the attributes of the subject person, it may be determined that the subject person has less than or equal to one half an hour per day of exposure to ultraviolet light based upon the image of FIG. 2.

Figure 3:
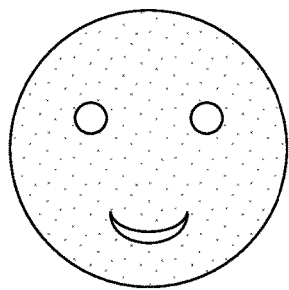

The RGB color of the portion of the image of FIG. 3 including the skin color of the subject person may be (240, 175, 150). This RGB color corresponds to the subject person having skin with a medium color, the medium color being indicative of some sun tan. In this example, based upon the attributes of the subject person, it may be determined that the subject person has two hours per day of exposure to ultraviolet light based upon the image of FIG. 3.

Figure 4:
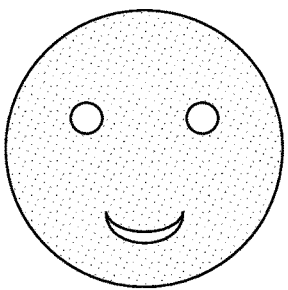

The RGB color of the portion of the image of FIG. 4 including the skin color of the subject person may be (160, 80, 40). This RGB color corresponds to the subject person having skin with a dark color, the dark color being indicative of a developed sun tan. In this example, based upon the attributes of the subject person, it may be determined that the subject person has four hours per day of exposure to ultraviolet light based upon the image of FIG. 4.

Figure 5:
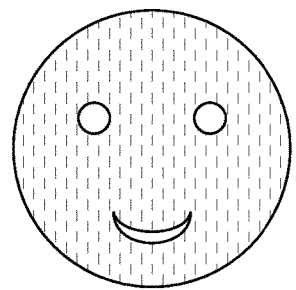

The RGB color of the portion of the image of FIG. 5 including the skin color of the subject person may be (255, 175, 150). This RGB color corresponds to the subject person having skin with a red color, the red color being indicative of a sunburn. In this example, based upon the attributes of the subject person, it may be determined that the subject person has eight hours per day of exposure to ultraviolet light based upon the image of FIG. 5.

Figure 6:
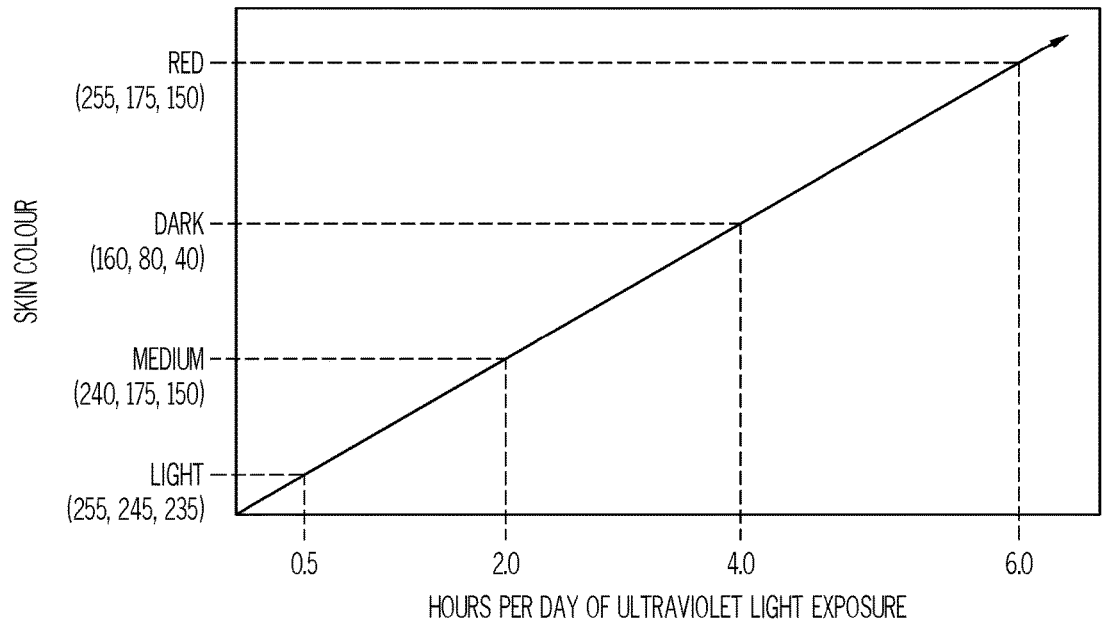
FIG. 6 illustrates an example of a chart for determining hours per day of ultraviolet light exposure based upon skin color of a subject person included within a recorded image.

FIG. 6 shows an example of a chart for determining hours per day of ultraviolet light exposure based upon skin color of a subject person included within a recorded image. An image of the subject person showing a light, medium, dark and red skin colors, having RGB values of (255, 245, 235), (240, 175, 150), (160, 80, 40), and (255, 175, 150) respectively, corresponds to 0.5, 2.0, 4.0 and 8.0 hours per day of ultraviolet light exposure, respectively. The chart of FIG. 6 is for a particular subject person, other persons may have other charts for relating skin color to levels of ultraviolet light exposure. The chart may be obtained empirically by monitoring the skin color of the subject person based upon known levels of ultraviolet light exposure, or the chart may be determined from attributes of the subject person. Attributes of the subject person that may be useful in determining the relationship between skin color and a level of ultraviolet light exposure include age, gender, hair color, eye color, skin type (see the Fitzpatrick scale for example which is known to those familiar with the art), and geographic origin (see the Von Luschan chromatic scale for example which is known to those familiar with the art).

Figure 8:
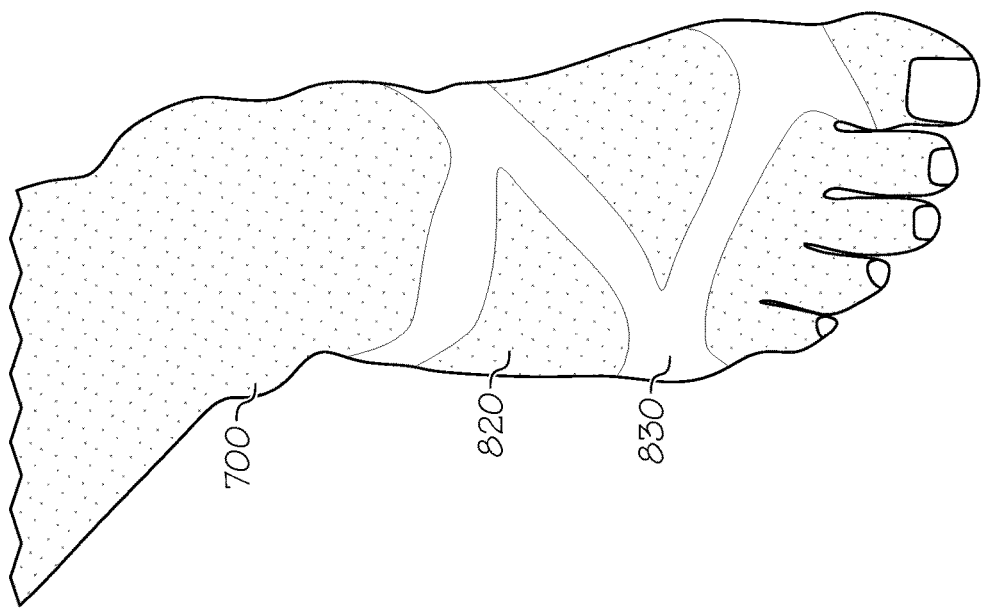
FIG. 7 and FIG. 8 illustrate an example of a social media image that may be used in another method for determining ultraviolet light exposure levels based upon skin color.
Figure 7:
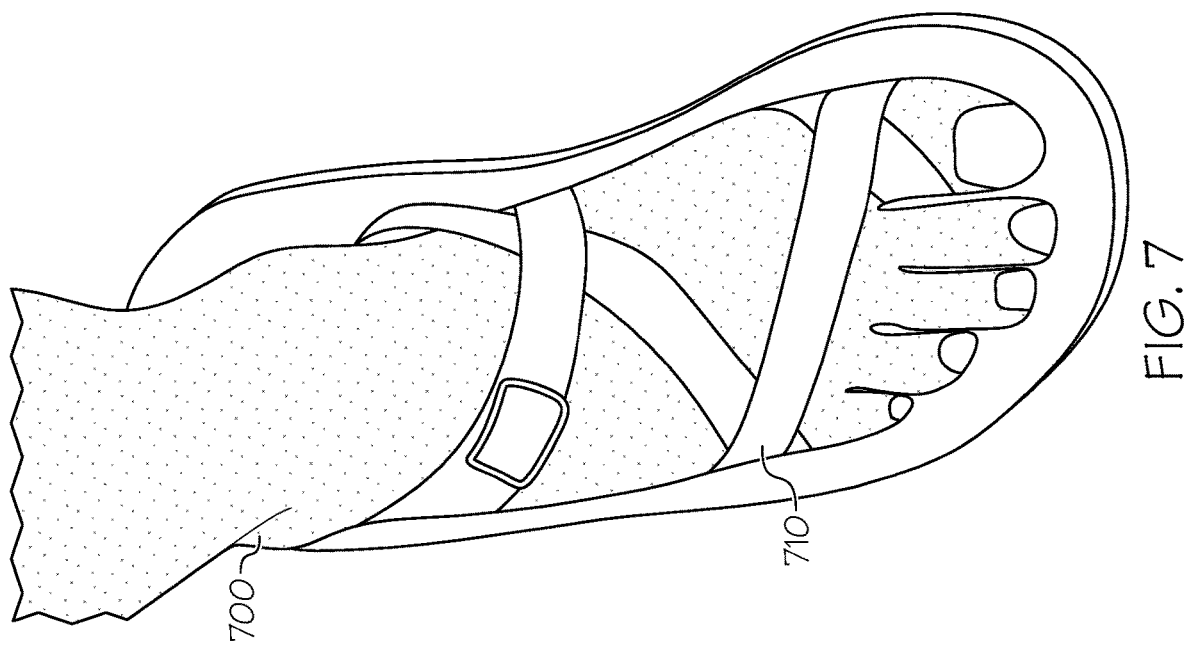

FIG. 7 and FIG. 8 illustrate an example of a social media image that may be used in another method for determining ultraviolet light exposure levels based upon skin color. The image of FIG. 7 shows a foot 700 of the subject person, wherein the subject person is wearing a sandal 710. FIG. 8 shows an image of the foot 700 of the subject person after the sandal is removed. FIG. 8 shows an image of the subject person having an exposed area of skin 820 having exposure to ultraviolet light because it was not covered by the sandal, and an unexposed area of skin 830 having less exposure to ultraviolet light than the exposed area of skin. In this example the color of the unexposed area may have an RGB value of (255, 245, 235) and the color of the exposed area may have an RGB value of (240, 175, 150). The unexposed area 830 may indeed have some exposure to ultraviolet light, albeit less exposure than the exposed area 820. Based upon the color difference it may be determined that the subject person has spent about 2 hours per day being exposed to ultraviolet light. This determination may be arrived at using a chart that shows that an unexposed skin color of (255, 245, 235) provides a characteristic relationship between hours per day of exposure to ultraviolet light and skin color, which in this example happens to correspond to the chart of FIG. 6. Note that an unexposed skin color that is different from the color of area 830 (255, 245, 235) may result in a different relationship between skin color and hours per day of exposure to ultraviolet light. Thus, in another example, a chart different from the chart of FIG. 6 may be used to determine the relationship between skin color and ultraviolet light exposure.

One potential advantage of the approach of processing the image of FIG. 8 is that the individual attributes of the person in the image, such as age, gender, hair color, eye color, skin type, and geographic origin need not be known. Thus, if the subject person is known to be related to the person in the image, then the ultraviolet light exposure of the person in the image may be either applied or indirectly equated to the ultraviolet light exposure of the subject person even though the subject person may not be included in the image. For example, if the person in the image is known to be a traveling companion of the subject person and the determination made that the person in the image received two hours per day of exposure to ultraviolet light, then the two hours per day of ultraviolet light exposure may be equated to the subject person based upon the assumption that the subject person and the companion participated in similar activities during their travels. This indirect data may be useful where more direct data relevant to the exposure of the subject person to ultraviolet light, such as the analysis of a photo of the subject person, is not available or can be used as supplemental data and may be assigned a lesser weight than an ultraviolet light exposure level determined from an image including the subject person. The relationship between the related person in the image and the subject person may be established in any of a number of ways including data from the social media database associated with the image that indicates that the person in the image is a travel companion of the subject person. For example, metadata may indicate that the image of FIG. 8 was recorded with a camera belonging to the subject person and the image data may have a caption such as "my companion's foot tan". The caption indicates the relationship with the subject person.

Figure 9:
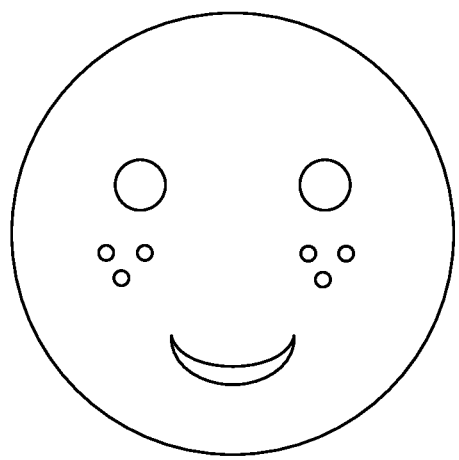
FIG. 9 and FIG. 10 illustrate an example of a social media image that may be used in another method for determining ultraviolet light exposure levels based upon freckling.
Figure 10:
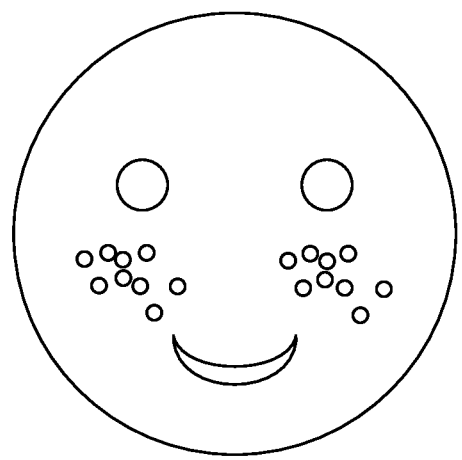

FIG. 9 and FIG. 10 illustrate an example of a social media image that may be used in another method for determining ultraviolet light exposure levels based upon freckling. Freckling increases as a person's exposure to ultraviolet light increases. FIG. 9 and FIG. 10 represent an image of the same person taken at different times. The image of the person recorded in FIG. 9 has less freckling than the image of the person recorded in FIG. 10. Thus, the person at the time of recording to FIG. 10 has received more average exposure to ultraviolet light than at the time of recording of FIG. 9. Such an analysis may be used in establishing an ultraviolet light exposure profile of the subject person. Furthermore, other visible characteristics of a person change with ultraviolet light exposure including hair color and skin blemishes. In certain persons, hair color tends to lighten with exposure to ultraviolet light. In certain persons, skin blemishes tend to increase with exposure to ultraviolet light. These changing characteristics may be used in determining an ultraviolet light exposure profile of a subject person. Similar to the analysis of skin color and ultraviolet light exposure rates, the personal attributes of the person recorded in the image may be used in determining the ultraviolet light exposure rate based upon changes in freckling, hair color and skin blemishes.

Figure 11:
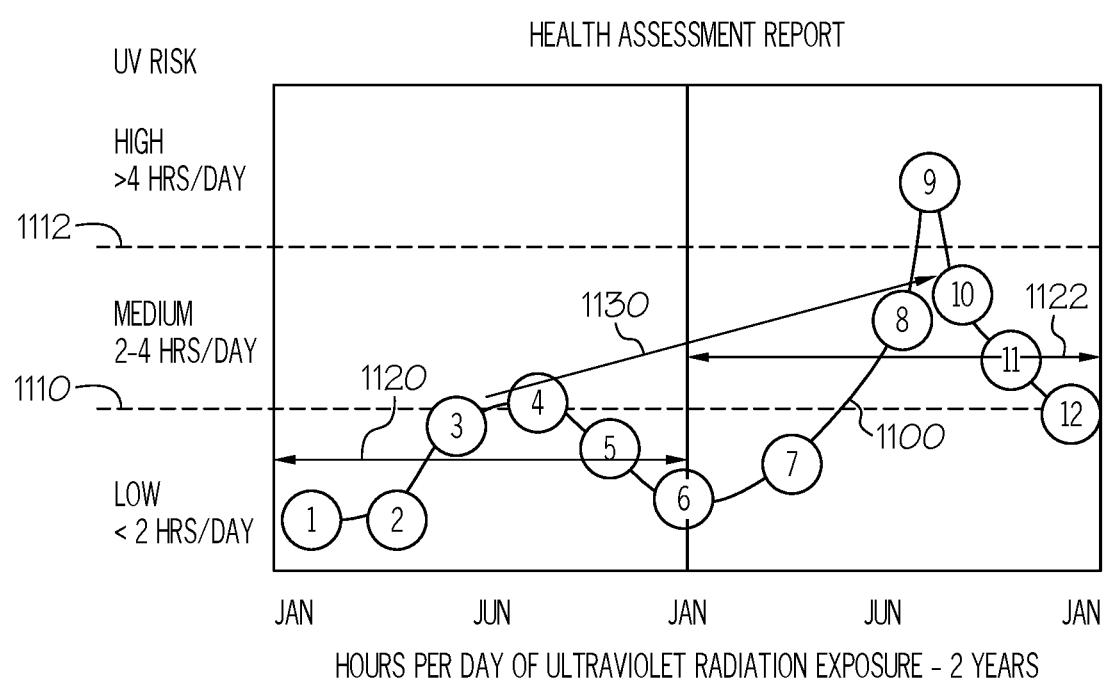
FIG. 11 illustrates an example of a graph of an ultraviolet light exposure profile of a subject person. The graph shows twelve data points over a period of two years.

FIG. 11 illustrates an example of a graph of an ultraviolet light exposure profile of a subject person. The graph shows twelve data points over a period of two years. The data points may be determined from data including images and metadata received from social media databases. Each data point represents a determined level of ultraviolet light exposure based upon data from events received from at least one social media database. In other examples, there may be significantly more (or less) data points accumulated over a significantly longer (or shorter) period of time and the data points may have an associated weight based upon the data received from the remote database. Line 1100 shows the determined ultraviolet light exposure profile of the subject person over the term of the graph. In this example, the line assumes that each data point is given the same weight and a smoothed line drawn between the data points. In other examples, where data points may be given varying weights, a line drawn between weighted data points using statistical analysis in a manner known to those familiar with the art. In one example, a data point determined from a high resolution image of the subject person with a good white balance calibration may be given greater weight than a data point determined from low resolution image of a related person with no white balance. The lower weight results from either the resolution of the image being poor, or the image may not include a significant white area in which to accurately calibrate the RGB color segmentation, or that the related person may have a different level of ultraviolet light exposure than the exposure determined for the related person at the data point.

In the example of FIG. 11, for a subject person having the attributes corresponding to the attributes of the subject person in the chart of FIG. 6, it has been determined that an average annual ultraviolet light exposure profile of less than two hours per day provides a low ultraviolet light exposure risk, as indicated by line 1110, while an average annual ultraviolet light exposure profile of more than four hours per day provides a high ultraviolet light exposure risk, as indicated by line 1120. Line 1120 is a graphical representation of an average exposure of ultraviolet light for the first year of the graph based upon the data points 1-6. The average is less than two hours per day and the ultraviolet light exposure risk is low. The health assessment report would then show that in the first year of the assessment the ultraviolet risk was low. However, image event 4 resulted in a determined exposure beyond two hours per day resulting in a determined medium risk for the subject person. If the social media data was analyzed at a point in time close to the occurrence of data point 4, then in response an alert could be generated by the health assessment report in response to warn of the increased risk level. The alert could be delivered electronically by email, text message, social media, or other electronic communication, or delivered by physical media such as the postal service. The alert could be delivered to the subject person or to a person associated with the subject person, such as a doctor, spouse, parent or companion of the subject person. Data points 5 and 6 show a reduced rate of ultraviolet light exposure towards the end of the first year. The reduced rate of exposure may have been a change in behavior of the subject person in response to the alert of data point 4, in response to a change in seasons, or any other of a number of reasons.

Figure 2:
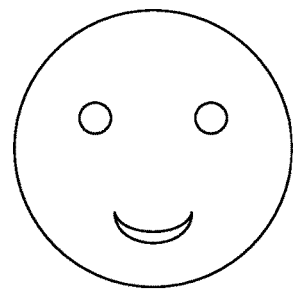
FIG. 2, FIG. 3, FIG. 4 and FIG. 5 illustrate examples of skin color of images of a subject person based upon exposure to ultraviolet light.

In the second year of the example of FIG. 11, the subject person starts the year with a low ultraviolet light exposure rate at data point 7, such as the person of FIG. 2. Data points 8, 10, 11 and 12 show a medium risk of ultraviolet light exposure, such as the person of FIG. 3 and FIG. 4. Data point 9 shows a very high level of ultraviolet light exposure and likely may likely be the result of a sunburn, such as the person of FIG. 5. Line 1122 is a graphical representation of an average exposure of ultraviolet light for the second year of the graph based upon the data points 7-12. The average is more than two hours per day and less than four hours per day, thus the ultraviolet light exposure risk is medium. The health assessment report would then show that in the second year of the assessment the ultraviolet risk was medium. Data point 9 resulted in a determined exposure beyond four hours per day resulting in a determined high risk for the subject person. If the social media data was analyzed at a point in time close to the occurrence of data point 9, then in response a health assessment report alert could be generated to warn of the high risk level. Similar to the discussion of data point 4, warning alerts can be generated for data points 8, 10, 11 and 12. Line 1130 shows the seasonal peak ultraviolet light exposure (excluding sunburn data point 9, which may be considered an exception in ultraviolet light exposure in the trend of the second year) increasing between the first and second years. The health assessment report may reflect that a finding that the seasonal peak exposure has increased as shown by line 1130 and is resulting in a medium level of risk. The health assessment report of the ultraviolet light exposure profile of line 1100 may also note a seasonal variation in that seasonally, the minimum exposure of data points 1, 2 and 5, 6, 7 appears a low risk from year to year, the peak exposure of data points 3, 4 and 8, 10, 11 show an increasing peak exposure on a seasonal basis. The health assessment report may also determine the ultraviolet light exposure risk over the duration of the ultraviolet light exposure profile, which in the example of FIG. 11 is two years, in other examples the duration may be shorter or significantly longer than two years, and may be for the lifetime of the subject person, depending on the data mined from the social media databases.

The health assessment report may be used to the benefit of the subject person in reducing the risks associated with ultraviolet light exposure. The health assessment report may go further to estimate a risk level for the subject person for certain cancers, including at least one of melanoma, basal cell carcinoma and squamous cell carcinoma, as well as other disorders related to ultraviolet light exposure and may be used for providing advice for the modification of behaviors to mitigate such risks. In arriving at the estimation, the health assessment report may weigh at least one additional factor including individual attributes including, moles, freckling, skin lesions, hair color, family history of melanoma, personal history of melanoma, age, gender, xeroderma pigmentosum, history of indoor tanning, and eye color of the subject person. Since the ultraviolet light exposure profile is mined from social media databases, the profile for each individual may be determined over a very long period of time with numerous data points, thereby increasing the accuracy of the health assessment report with little investment in time by the subject person in the gathering and/or provisioning of data for the report. When adopted on a large scale, the health assessment report for a larger segment of the population can help reduce the significant burdens skin cancer and related abnormalities places upon the health of the population.

Figure 12:
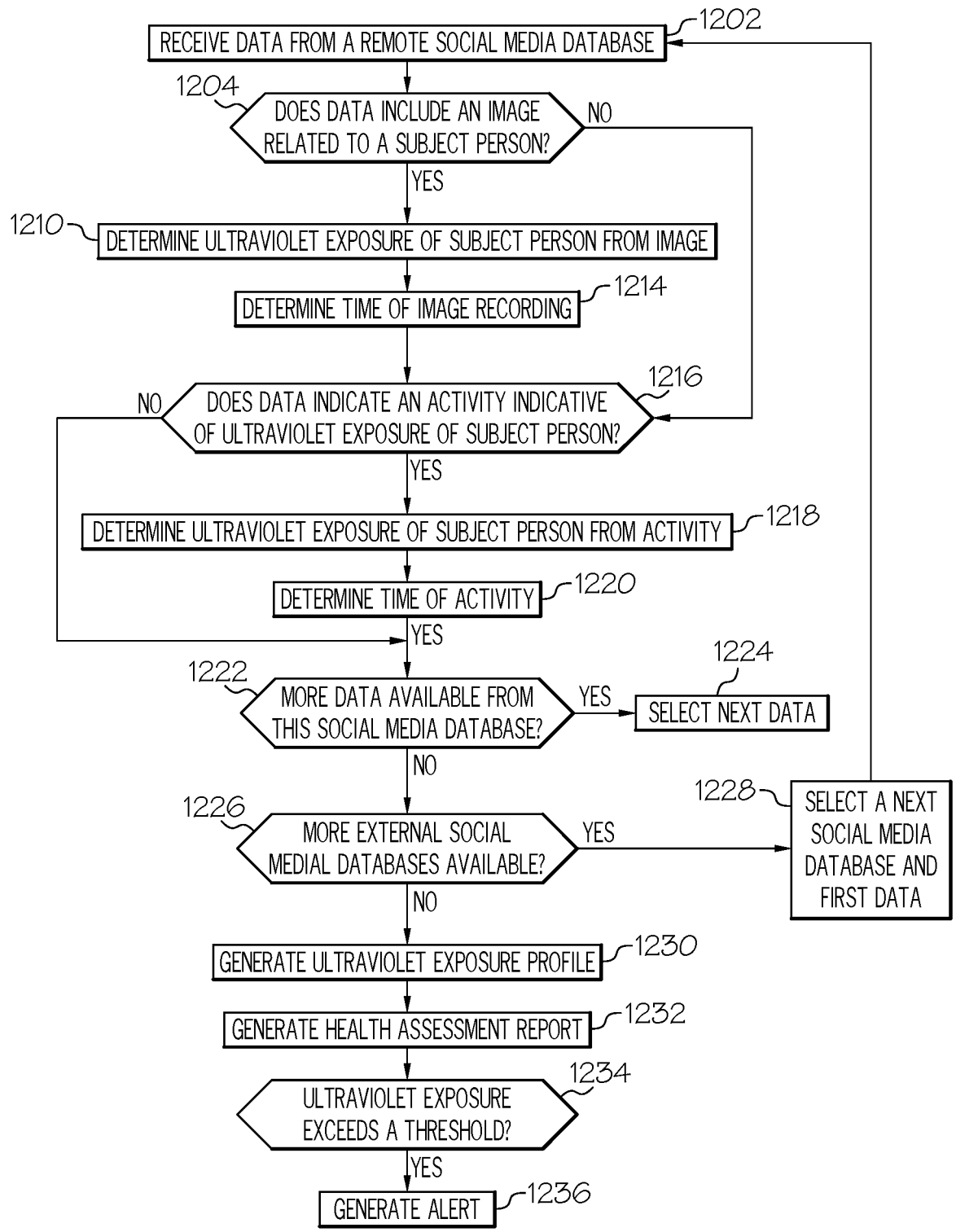
FIG. 12 illustrates an example of a representative flow diagram of a process for generating a health assessment report for a subject person based upon an ultraviolet light exposure profile analyzed from a multiplicity of data points received from social media databases.

FIG. 12 illustrates an example of a representative flow diagram of a process for generating a health assessment report for a subject person based upon an ultraviolet light exposure profile analyzed from a multiplicity of data points received from social media databases. Step 1202 receives data from a remote social media database and step 1204 determines if the data includes an image related to the subject person. The image may include the subject person or may include an image of a person related to a subject person. If so, step 1210 then determines the ultraviolet light exposure level of the subject person from the image, and step 1214 determines a time of the image recording. The time of image recording may be determined by a timestamp in metadata associated with the image or may be included in other data from the social media database. If the data does not include an image related to the subject person in step 1204, then step 1216 determines if the data indicates an activity indicative of ultraviolet light exposure of the subject person, as previously described. If so, step 1218 then determines the ultraviolet light exposure level of the subject person based upon the activity and step 1220 determines the time of the activity. An example of such an activity may be a calendar appointment showing an activity that may involve exposure to ultraviolet light. Then from either steps 1204, 1216 or 1220, step 1222 determines if more data is available from the currently selected social media database. If more data is available, then step 1224 selects the next data and returns to step 1202. If the currently selected social media database is mined, then step 1226 determines if another social media database should be examined, and if so selects the next social media database at step 1228 selects the first data portion of the next social media database and returns to step 1202. If all databases have been examined, then step 1226 proceeds to step 1230 to generate an ultraviolet light exposure profile. FIG. 11 shows an example of at least a portion of an ultraviolet light exposure profile. Then step 1232 generates health assessment report based upon the ultraviolet light exposure profile and if an exposure threshold is exceeded, an alert may be generated. The health assessment report may include analysis of a risk of skin cancer of the selected person as well as advise of certain behaviors that may be beneficial or detrimental based upon data minded from social media databases. The alert may include a timely notice of a substantial risk of over exposure to ultraviolet light.

Figure 13:
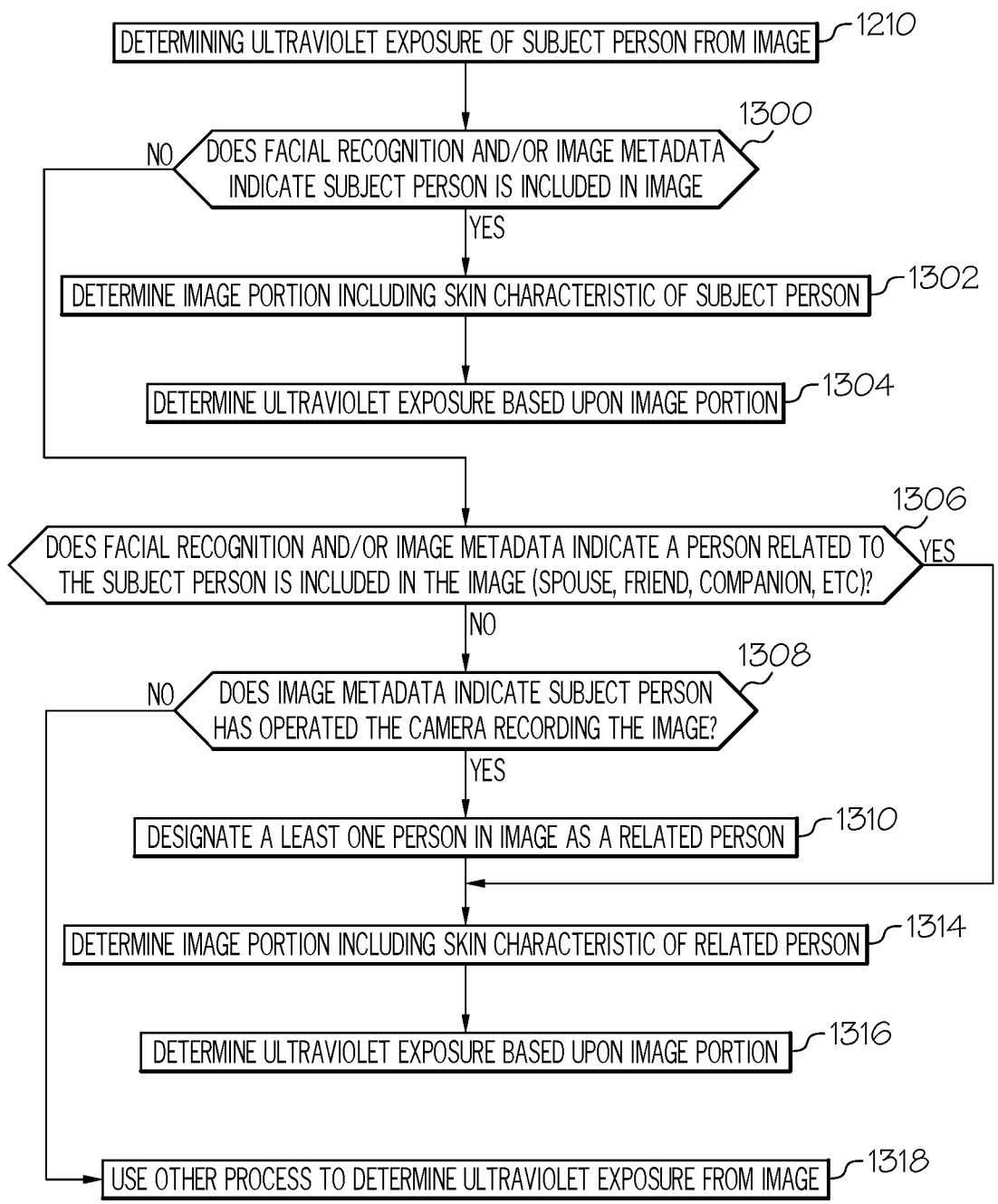
FIG. 13 illustrates an example of a representative flow diagram of a process for determining ultraviolet light exposure of a subject person from an image.

FIG. 13 illustrates an example of a representative flow diagram of a process for determining ultraviolet light exposure of a subject person from an image. FIG. 13 corresponds to an example of a more detailed description of the process of step 1210 of FIG. 12. Step 1300 determines if facial recognition and/or metadata indicates the subject person is included in the image that was received from the social media database that is currently being analyzed. If so, step 1302 determines the portion of the image including a skin characteristic of the subject person for analysis. The portion of skin may be any portion, for example may include the forehead of the subject person. Then step 1304 determines the ultraviolet light exposure based upon the selected image portion, which may include using the graph of FIG. 6 to relate skin color to an ultraviolet light exposure level. If the subject person is not included in the image at step 1302, then step 1306 determines if a person related to the subject person is included in the image. The related person may include a spouse, friend or companion of the subject person. The presence of the related person in the image may be determined by analyzing metadata associated with the image, or by performing facial recognition on the image to determine if the face of the related person is included in the image or other process for determining a relationship with the subject person. Otherwise step 1308 determines if the image was recorded with a camera associated with the subject person, if so step 1310 designates a person in the image as a related person. Step 1314 determines an image portion including a skin characteristic of the related person and step 1316 determines the ultraviolet light exposure of the subject person based upon the ultraviolet light exposure of the related person included in the image. Otherwise, step 1318 may use other processes to determine ultraviolet light exposure from the image. For example the image may be one of a series of sunny images of an outdoor tennis match, for example, taken by a camera associated with the subject person. In response, it may be determined that the subject person received ultraviolet light exposure for the duration of the series of photographs. Another example would be to analyze changes in hair color, freckling or skin blemishes to determine ultraviolet light exposure.

Figure 14:
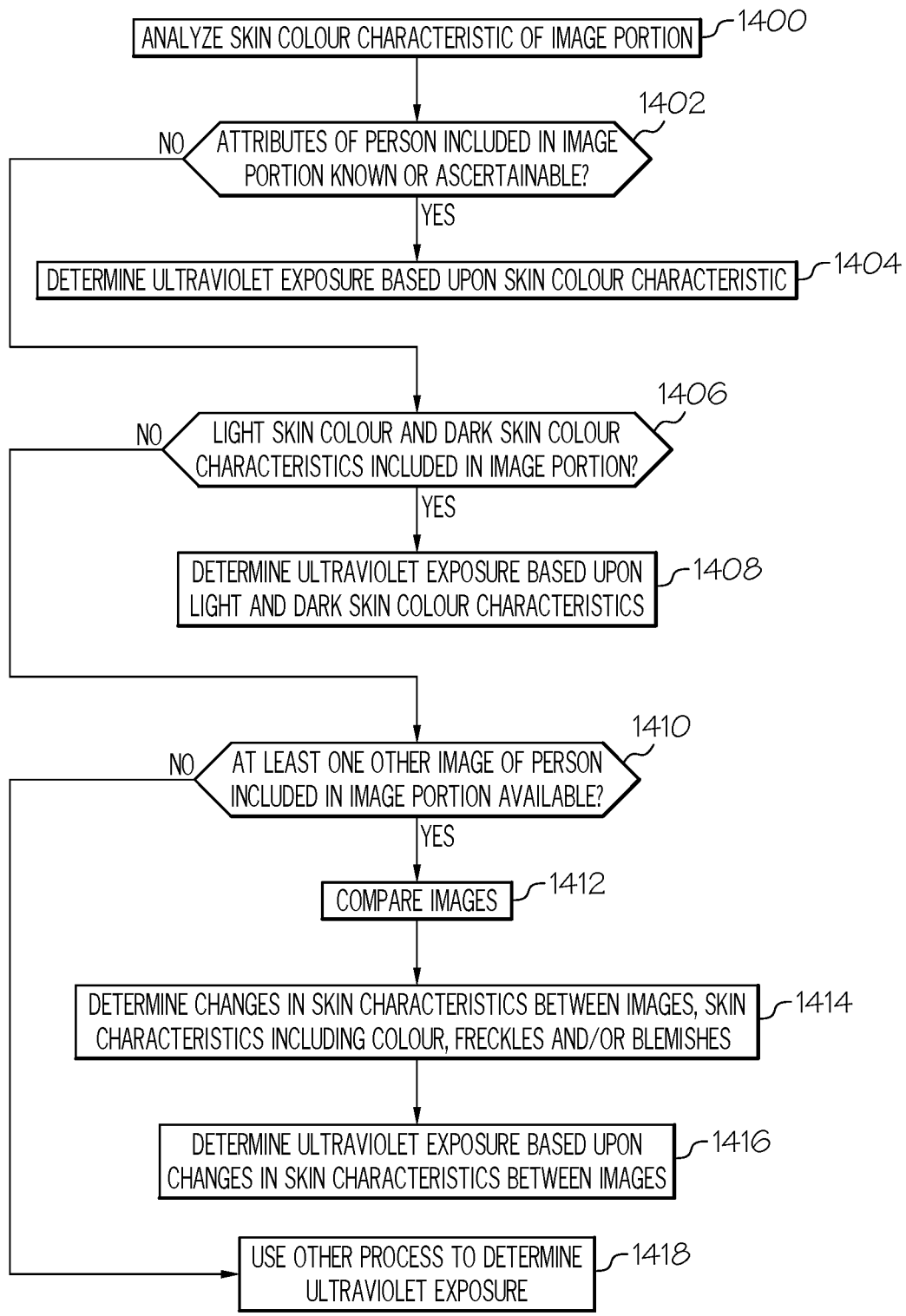
FIG. 14 illustrates an example of a representative flow diagram of a process for determining ultraviolet light exposure by analyzing skin color of an image.

FIG. 14 illustrates an example of a representative flow diagram of a process for determining ultraviolet light exposure by analyzing skin color included within an image. The skin color may be that of the subject person or a person related to the subject person. The flow diagram enters at step 1400 and step 1402 determines if attributes of a person included in the image portion are known or ascertainable and if so, step 1404 determines the ultraviolet light exposure based upon the skin color. FIG. 6 represents a graph for determining an ultraviolet light exposure level of person with known attributes based upon skin color. The person may be the subject person or a related person. The attributes may be already determined or ascertainable using data from social media databases and include age, gender, hair color, eye color, skin type, and geographic origin. If the attributes are not known, step 1406 determines if a light skin color and a dark skin color characteristic are included in the image, similar to the example image of FIG. 8. If so, step 1408 determines ultraviolet light exposure based upon the dark and light skin color characteristics as previously described with respect to FIG. 8. Otherwise, step 1410 determines if at least one other image of the person included in the image portion is available. If so, then the images are compared in step 1412 and the changes in skin characteristics including skin color, freckling, and/or blemishes are analyzed in step 1404 to determine ultraviolet light exposure in step 1416. For example, if one photo has a person with a skin color corresponding to light skin color of area 830 of FIG. 8 and another photo has the person with a skin color corresponding to the dark area 820 of FIG. 8, then the graph of FIG. 6 may be used to determine ultraviolet light exposure level for the image of the person with a skin color corresponding to the darker area. Otherwise, other approaches may be used to analyze skin characteristics to determine ultraviolet light exposure in step 1418 while remaining within the scope of this description.

The respective implementations of the present disclosure can be carried out in any appropriate mode, including hardware, software, or firmware stored on a storage media and executed computer storage program product, or combination thereof. Alternatively, it is possible to at least partially carry out the implementation of the present disclosure as computer software executed on one or more data processors and/or a digital signal processor. The components and modules or processes of the implementation of the present disclosure can be implemented physically, functionally and logically in any suitable manner. Indeed, the function can be realized in a single member or in a plurality of members, or as a part of other functional members. Thus, it is possible to implement the implementation of the present disclosure in a single member or distribute it physically and functionally between different members and a processor.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described herein with reference to flowchart illustrations flow diagrams and/or block diagrams of methods, apparatus (systems) and computer program products according to implementations of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the computer or other programmable data processing apparatus, create means for implementing the functions/acts specified in the blocks of the flowchart illustrations and/or block diagrams.

These computer program instructions may also be stored in a computer readable medium that can direct a computer or other programmable data processing apparatus to function in a particular manner, such that the instructions stored in the computer readable medium produce an article of manufacture including instruction means which implement the functions/acts specified in the blocks of the flowchart illustrations and/or block diagrams.

The computer program instructions may also be loaded onto a computer or other programmable data processing apparatus to cause a series of operational steps to be performed on the computer or other programmable data processing apparatus to produce a computer implemented process such that the instructions which execute on the computer or other programmable apparatus provide processes for implementing the functions/acts specified in the blocks of the flowchart illustrations and/or block diagrams.

The present disclosure is described by use of detailed illustration of the implementations of the present disclosure, and these implementations are provided as examples and do not intend to limit the scope of the present disclosure. Although these implementations are described in the present disclosure, modifications and variations on these implementations will be apparent to those of ordinary skill in the art. Therefore, the above illustration of the exemplary implementations does not confine or restrict the present disclosure. Other changes, substitutions and modifications are also possible, without departing from the scope of the description and the appended claims.

What is claimed is:

1. A method comprising:
   receiving a multiplicity of images from an at least one remote database;
   analyzing, by a digital processing machine, the multiplicity of images to determine an ultraviolet light exposure profile of a subject person; and
   the analyzing further includes:
   determining a presence of a related person within the multiplicity of images;
   determining a related skin characteristic of the related person for each of the multiplicity of images; and
   determining an ultraviolet light exposure level for the related person, and
   the determining the ultraviolet light exposure profile of the subject person further includes determining the ultraviolet light exposure profile of the subject person based upon the ultraviolet light exposure level of the related person.

2. The method according to claim 1 wherein the receiving further includes
   receiving a first plurality of the multiplicity of images from a first remote database including a first social media database; and
   receiving a second plurality of the multiplicity of images from a second remote database including a second social media database different from the first social media database.

3. The method according to claim 1 wherein the subject person has a skin characteristic that varies based upon exposure to ultraviolet light, and further includes:
   generating a health assessment report for the subject person based upon the ultraviolet light exposure profile, wherein the related person having a relationship with the subject person has the related skin characteristic that varies based upon exposure to ultraviolet light;
   the receiving further receives metadata associated with the multiplicity of images, the metadata including a timestamp associated with each of the multiplicity of images indicative of a time of image recording, and
   the analyzing further includes
   determining a presence of the subject person within a plurality of images of the multiplicity of images, and
   determining the skin characteristic of the subject person in each of the plurality of images in which the subject person is present, and
   the generating generates the health assessment report based upon the skin characteristic and the timestamp from each of the plurality of images in which the subject person is present.

4. The method according to claim 3 wherein the skin characteristic includes at least one of skin color, skin freckling, skin blemishes and skin lesions.

5. The method according to claim 3 wherein the skin characteristic includes skin color and the analyzing determines the ultraviolet light exposure profile based upon at least one individual attribute associated with the subject person and the skin color, the at least one individual attribute indicative of a relationship between skin color and exposure to ultraviolet light of the subject person, the individual attribute including at least one of age, gender, hair color, eye color, skin type, and geographic origin.

6. The method according to claim 3 wherein the skin characteristic includes skin color and the multiplicity of images includes an image of the subject person having an exposed area of skin having exposure to ultraviolet light and an unexposed area of skin having less exposure to ultraviolet light than the exposed area of skin and
the analyzing further includes
determining a first skin color of the exposed area of skin,
determining a second skin color of the unexposed area of skin, and
determining the ultraviolet light exposure profile includes determining the ultraviolet light exposure profile based upon the first skin color and the second skin color.

7. The method according to claim 3 wherein the subject person has a hair color that varies based upon exposure to ultraviolet light, and further includes:
generating a health assessment report for the subject person based upon the ultraviolet light exposure profile, wherein the related person having a relationship with the subject person has the related skin characteristic that varies based upon exposure to ultraviolet light;
the analyzing further includes determining the hair color of the subject person for each of the plurality of images in which the subject person is present, and
the generating generates the health assessment report further based upon the hair color and the timestamp of each of the plurality of images in which the subject person is present.

8. The method according to claim 3 further includes:
generating a health assessment report for the subject person based upon the ultraviolet light exposure profile, wherein the related person having a relationship with the subject person has the related skin characteristic that varies based upon exposure to ultraviolet light;
wherein the generating further generates the health assessment report based upon at least one additional factor including moles, freckling, hair color, family history of melanoma, personal history of melanoma, age, gender, xeroderma pigmentosum, history of indoor tanning, and eye color of the subject person.

9. The method according to claim 3 wherein the metadata includes information indicative of a behavior of the subject person, the behavior of the subject person is indicative of exposure to ultraviolet light and the analyzing further analyzes the metadata to determine the behavior of the subject person in determining the ultraviolet light exposure profile of the subject person.

10. The method according to claim 9 wherein the behavior of the subject person includes at least one of a vacation location, participation in an outdoor sport, an ultraviolet tanning salon visit, and a chemical spray tanning salon visit.

11. The method according to claim 3 wherein the skin characteristic varies on a seasonal basis with a potential for an increased ultraviolet light exposure during a first season and a decreased ultraviolet light exposure during a second season and further wherein the analyzing determines the ultraviolet light exposure profile based upon seasonal variation of the skin characteristic.

12. The method according to claim 1 further includes:
generating a health assessment report for the subject person based upon the ultraviolet light exposure profile, wherein the related person having a relationship with the subject person has the related skin characteristic that varies based upon exposure to ultraviolet light;
wherein the health assessment report includes determining a risk level of a skin cancer, the skin cancer including at least one of melanoma, basal cell carcinoma and squamous cell carcinoma.

13. The method according to claim 12 further comprising the step of generating an alert based upon the risk level exceeding a threshold.

14. A computer storage program product comprising:
a non-transitory computer readable storage medium readable by a processing circuit and storing instructions for execution by the processing circuit configured to perform a method comprising:
receiving a multiplicity of images from an at least one remote database;
analyzing the multiplicity of images to determine an ultraviolet light exposure profile of a subject person; and
the analyzing further includes:
determining a presence of a related person within the multiplicity of images;
determining a related skin characteristic of the related person for each of the multiplicity of images; and
determining an ultraviolet light exposure level for the related person, and
the determining the ultraviolet light exposure profile of the subject person further includes determining the ultraviolet light exposure profile of the subject person based upon the ultraviolet light exposure level of the related person.

15. The computer storage program product according to claim 14 further includes:
generating a health assessment report for the subject person based upon the ultraviolet light exposure profile, wherein the related person having a relationship with the subject person has the related skin characteristic that varies based upon exposure to ultraviolet light;
wherein the subject person has a skin characteristic that varies based upon exposure to ultraviolet light, and
the receiving further receives metadata associated with the multiplicity of images, the metadata including a timestamp associated with each of the multiplicity of images indicative of a time of image recording, and
the analyzing further includes
determining a presence of the subject person within a plurality of images of the multiplicity of images, and
determining the skin characteristic of the subject person in each of the plurality of images in which the subject person is present, and
the generating generates the health assessment report based upon the skin characteristic and the timestamp from in each of the plurality of images in which the subject person is present.

16. The computer storage program product according to claim 15 wherein the skin characteristic includes skin color and the multiplicity of images includes an image of the subject person having an exposed area of skin having exposure to ultraviolet light and an unexposed area of skin having less exposure to ultraviolet light than the exposed area of skin and the analyzing further includes
determining a first skin color of the exposed area of skin,
determining a second skin color of the unexposed area of skin, and
determining the ultraviolet light exposure profile includes determining the ultraviolet light exposure profile based upon the first skin color and the second skin color.

17. The computer storage program product according to claim 15 wherein a related person having a relationship with the subject person has a related skin characteristic that varies based upon exposure to ultraviolet light, and the analyzing further includes:
- determining a presence of the related person within the multiplicity of images;
- determining the related skin characteristic of the related person for each of the multiplicity of images; and
- determining an ultraviolet light exposure level for the related person, and
- determining the ultraviolet light exposure profile of the subject person further includes determining the ultraviolet light exposure profile of the subject person based upon the ultraviolet light exposure level of the related person.

18. A device comprising:
- a data receiver configured to receive a multiplicity of images recorded with visible light, the multiplicity of images received from a plurality of social media databases;
- a subject person identifier configured to analyze the multiplicity of images to identify a plurality of subject person images including a subject person having a skin color that varies with exposure to ultraviolet light;
- a skin color determiner configured to determine a skin color of the subject person within each of the subject person images;
- an ultraviolet light exposure determiner configured to generate a multiplicity of data points corresponding to the multiplicity of images, each data point corresponding to an ultraviolet light exposure level for each of the subject person images determined based upon the skin color of the subject person within each of the subject person images; and
- a multiple photo analyzer configured to generate an ultraviolet light exposure profile for the subject person based upon the multiplicity of data points.

19. The device according to claim 18 further includes:
- generating a health assessment report for the subject person based upon the ultraviolet light exposure profile, wherein the related person having a relationship with the subject person has a related skin characteristic that varies based upon exposure to ultraviolet light;
- wherein a related person having a relationship with the subject person has a related skin color that varies based upon exposure to ultraviolet light, and further wherein
- the subject person identifier is further configured analyze the multiplicity of images to identify at least one related person image including the related person,
- the skin color determiner configured to determine a skin color of the related person within at least one related person image, and
- the ultraviolet light exposure determiner is further configured to generate at least one of the multiplicity of data points corresponding to an ultraviolet light exposure level of the at least one related person image determined based upon the skin color of the related person within the at least one related person image,
- wherein the health assessment report includes an ultraviolet light exposure risk assessment for the subject person based at least in part upon the determined ultraviolet light exposure level of the related person.

\* \* \* \* \*